US008102532B2

(12) United States Patent  
Kosterev et al.

(10) Patent No.: US 8,102,532 B2
(45) Date of Patent: Jan. 24, 2012

(54) RESONANT OPTOTHERMOACOUSTIC DETECTION OF OPTICAL ABSORPTION

(75) Inventors: Anatoliy A. Kosterev, Pearland, TX (US); Sergei M. Bachilo, Houston, TX (US)

(73) Assignee: William Marsh Rice University, Houston, TX (US)

( * ) Notice: Subject to any disclaimer, the term of this patent is extended or adjusted under 35 U.S.C. 154(b) by 424 days.

(21) Appl. No.: 12/347,470

(22) Filed: Dec. 31, 2008

(65) Prior Publication Data

US 2009/0174884 A1 Jul. 9, 2009

Related U.S. Application Data

(60) Provisional application No. 61/018,590, filed on Jan. 2, 2008.

(51) Int. Cl.
*G01N 21/00* (2006.01)

(52) U.S. Cl. .................... 356/437; 250/343

(58) Field of Classification Search .................... None
See application file for complete search history.

(56) References Cited

U.S. PATENT DOCUMENTS

| | | | | |
|---|---|---|---|---|
| 3,902,355 | A * | 9/1975 | Weisser | 73/384 |
| 4,897,541 | A * | 1/1990 | Phillips | 250/227.21 |
| 7,183,553 | B1 * | 2/2007 | Willing et al. | 250/339.13 |
| 7,245,380 | B2 | 7/2007 | Kosterev | |
| 2006/0266109 | A1 * | 11/2006 | DiFoggio | 73/152.55 |

OTHER PUBLICATIONS

Hartung, C., et al., "Investigation of the properties of an optothermal detector," Sov. J. Quantum Electron., Aug. 1978, pp. 1035-1037, vol. 8, No. 8, © 1979 American Institute of Physics.

Hartung, C., et al., "Laser spectroscopy by an optothermal detector (OT)," Ferroelectrics, 1981, pp. 21-26, vol. 34, Gordon and Breach, Science Publishers, Inc., USA.

Iqbal, Khalid, "Sub-doppler excited molecule energy transfer spectroscopy," Applied Physics B, 1982, pp. 153-156, vol. 27, Springer-Verlag.

Kosterev, Anatoliy A., "Applications of quartz tuning forks in spectroscopic gas sensing," Review of Scientific Instruments, 2005, pp. 043105-1 to 043105-9, vol. 76, American Institute of Physics.

Pickrell, Gary, et al., "Stochastic holey optical fibers for gas sensing applications," Sensors for Harsh Environments III, 2007, pp. 67570D-1 to 67570D-9, vol. 6757, Proc. of SPIE.

Provisional patent application entitled "Resonant optothermoacoustic detection of optical absorption," by Anatoliy A. Kosterev, et al., filed Jan. 2, 2008 as U.S. Appl. No. 61/018,590.

Rosengren, Lars-Göran, "An opto-thermal gas concentration detector," Infrared Physics, 1973, pp. 173-182, vol. 13, Pergamon Press, Great Britain.

* cited by examiner

*Primary Examiner* — Gregory J Toatley
*Assistant Examiner* — Juan D Valentin
(74) *Attorney, Agent, or Firm* — Conley Rose, P.C.; Rodney B. Carroll

(57) ABSTRACT

A device comprising an acoustic detector, one or more thermal sensing elements coupled to the acoustic detector, and a light source. A method comprising directing a beam of light at a wavelength at or near one or more thermal sensing elements, wherein the thermal sensing elements are coupled to an acoustic detector, determining a resonance frequency of the acoustic detector, wherein the acoustic detector is coupled to one or more of the thermal sensing elements, and measuring the response of the acoustic detector to detect optical radiation absorption proximate to or at the surface of one or more thermal sensing elements.

20 Claims, 5 Drawing Sheets

A

RESONANT OPTOTHERMOACOUSTIC DETECTION OF OPTICAL ABSORPTION

CROSS-REFERENCE TO RELATED APPLICATIONS

The present application claims priority to U.S. Provisional Patent Application Ser. No. 61/018,590 filed Jan. 2, 2008 by Kosterev et al. and entitled "Resonant Optothermoacoustic Detection of Optical Absorption," which is incorporated herein by reference as if reproduced in its entirety.

STATEMENT REGARDING FEDERALLY SPONSORED RESEARCH OR DEVELOPMENT

Not Applicable.

BACKGROUND

1. Field of the Invention

This invention relates generally to the field of spectroscopy. More specifically, the invention relates to a method and device for resonant optothermoacoustic (ROTA) spectroscopy.

2. Background of the Invention

Photoacoustic spectroscopy (PAS) is an analytical method that involves stimulating a sample with modulated light and detecting the resulting sound waves emanating from the sample. A photoacoustic measurement can be made as follows. Methods and devices related to detecting photoacoustic signals in a fluid are discussed at length in U.S. Pat. No. 7,245,380 to Kosterev, which is incorporated herein in its entirety. First, light is used to stimulate molecules within a sample. Such stimulation can include, for example, absorption of the light by the molecule to change an energy state of the molecule. As a result, the stimulated molecule enters an excited state. Optical excitation is followed by the energy transfer processes (relaxation) from the initially excited molecular energy level to other degrees of freedom, in particular translational motion of the fluid molecules. During such relaxation, heat, light, volume changes and other forms of energy can dissipate into the environment surrounding the molecule. Such forms of energy cause expansion or contraction of materials within the environment. As the materials expand or contract, sound waves are generated.

In order to produce identifiable sound waves, or photoacoustic signals, the light is pulsed or modulated at a specific resonant acoustic or modulation frequency f (having a modulation period 1/f), sometimes also described by the cyclic frequency $\Omega=2\pi f$. The sample environment may be enclosed and may be constructed to resonate at the modulation frequency. An acoustic detector mounted in acoustic communication with the sample environment can detect changes occurring as a result of the modulated light stimulation of the sample. Because the amount of absorbed energy is proportional to the concentration of the absorbing molecules, the acoustic signal can be used for concentration measurements.

In typical PAS, a resonant acoustic cavity or sample cell with a quality factor Q is used to isolate and amplify sound wave signals, thereby increasing sensitivity of detection. The light intensity or wavelength is modulated at f. The absorbed energy is accumulated in the acoustic mode of the sample cell during Q oscillation periods. Hence, the acoustic signal is proportional to the effective integration or energy accumulation time t, where $t=Q/f$. Most often the Q factor is in the range 40-200 and f=1,000-4,000 Hz. Thus, in a non-limiting example, Q may equal 70 and f=1250 Hz, with the result that t=0.056 s.

BRIEF SUMMARY

Disclosed herein is a device comprising an acoustic detector, one or more thermal sensing elements coupled to the acoustic detector, and a light source.

Also, disclosed herein is a method comprising directing a beam of light at a wavelength at or near one or more thermal sensing elements, wherein the thermal sensing elements are coupled to an acoustic detector, determining a resonance frequency of the acoustic detector, wherein the acoustic detector is coupled to one or more of the thermal sensing elements, and measuring the response of the acoustic detector to detect optical radiation absorption proximate to or at the surface of one or more thermal sensing elements.

Methods and devices for resonant optothermoacoustic spectroscopy are disclosed herein. The methods and devices utilize optothermal and photoacoustic principles to enhance sensitivity for the detection of chemical species. Further aspects and advantages of the methods and devices will be described in further detail below.

Advantages of the ROTA detection over conventional optothermal spectroscopy include: possibility to operate the sensor at higher modulation frequency compared to pyroelectric or other purely thermal detectors, thus reducing 1/f noise; potentially extended interaction length in the implementation of the embodiments shown in FIGS. 4 and 5; larger flexibilities in terms of materials interacting with molecules and radiation and sensor element geometries. In various embodiments, the methods, systems, and devices disclosed herein also provide the advantages of: resonant signal enhancement, zero background, lower thermal mass, ease of alignment, the potential for room temperature operation, and lower cost when compared to optothermal spectroscopy.

Advantages of the ROTA detection over conventional photoacoustic spectroscopy or quartz-enhanced photoacoustic spectroscopy (QEPAS) include: less signal dependence on the V-T relaxation processes in the gas under study; possibility of operating at lower pressures for better spectral resolution in gases, including sub-Doppler resolution.

The foregoing outlines rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION OF THE PREFERRED EMBODIMENTS

In an embodiment, a method of detecting weak absorption of optical radiation combines approaches of optothermal and photoacoustic detection. Without being limited by theory, optothermal detection is a spectroscopic technique where the energy input into gas or other media caused by absorption of an optical radiation is measured directly by means of a thermal detector, usually using pyroelectric detectors or bolometers. A fraction of the absorbed energy is transferred to the thermal detector by heat conduction or molecular diffusion. In contrast, photoacoustic detection is based on detection of sound waves generated in a media upon absorption of the modulated optical radiation.

In general, the disclosed method of ROTA detection is based upon the following processes: (1) excitation of a fluid region or object under study by a modulated optical radiation, where the energy input frequency is equal to the resonant mechanical frequency of the detector; (2) energy transfer from the optically excited region or object to the sensing element via thermal conductivity, molecular diffusion, or free molecular motion; (3) periodic heating and the related thermal expansion of the sensing element, (4) excitation of resonant mechanical vibrations in a detector (preferably a piezoelectric crystal) being the same as the sensing element or having a rigid mechanical connection to the sensing element; (5) measuring the vibration amplitude of the detector, preferably by means of its piezoelectric response. Other possible options include interferometric and capacitive measurements of the detector vibrations. In various embodiments, such methods may be carried out with a device or apparatus as shown in FIGS. 2-5.

Figure 1:
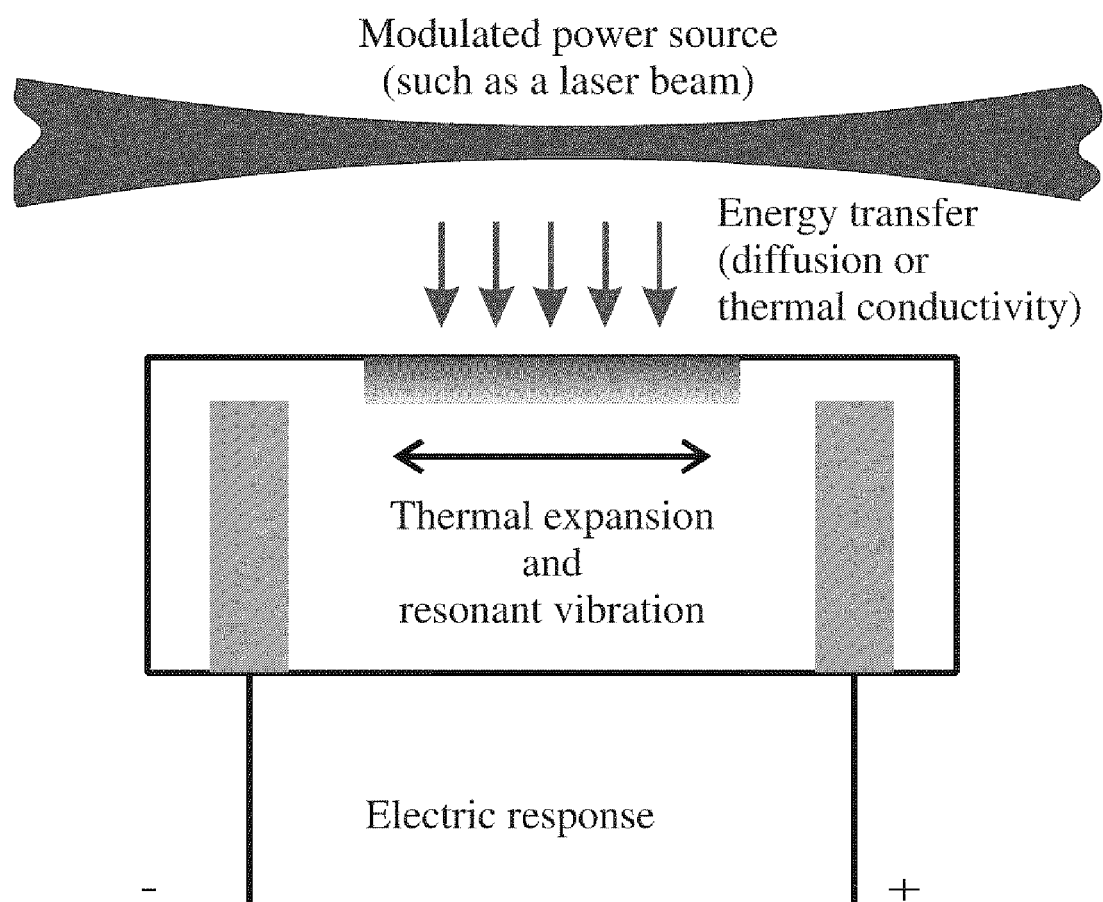
FIG. 1 illustrates the principles behind ROTA spectroscopy.

The principal of ROTA operation is illustrated in FIG. 1 using absorption in a fluid as an example. Without being limited by theory, if there is a periodic energy input into a fluid, a diffusion wave and/or a heat wave will be generated in the vicinity of the excited fluid area, followed by energy dissipation. This wave will reach a small sensing element positioned nearby and result in its periodic heating and cooling, causing the local temperature modulation and related periodic deformation. The structural deformation in the sensing element (the element can also be a region on the detector) will be enhanced by the resonance effect in the detector (such as a resonant piezoelectric crystal) and converted to electrical signal via piezoelectric effect. The proposed method for some applications combines advantages of the related optothermal and QEPAS techniques.

Figure 2:
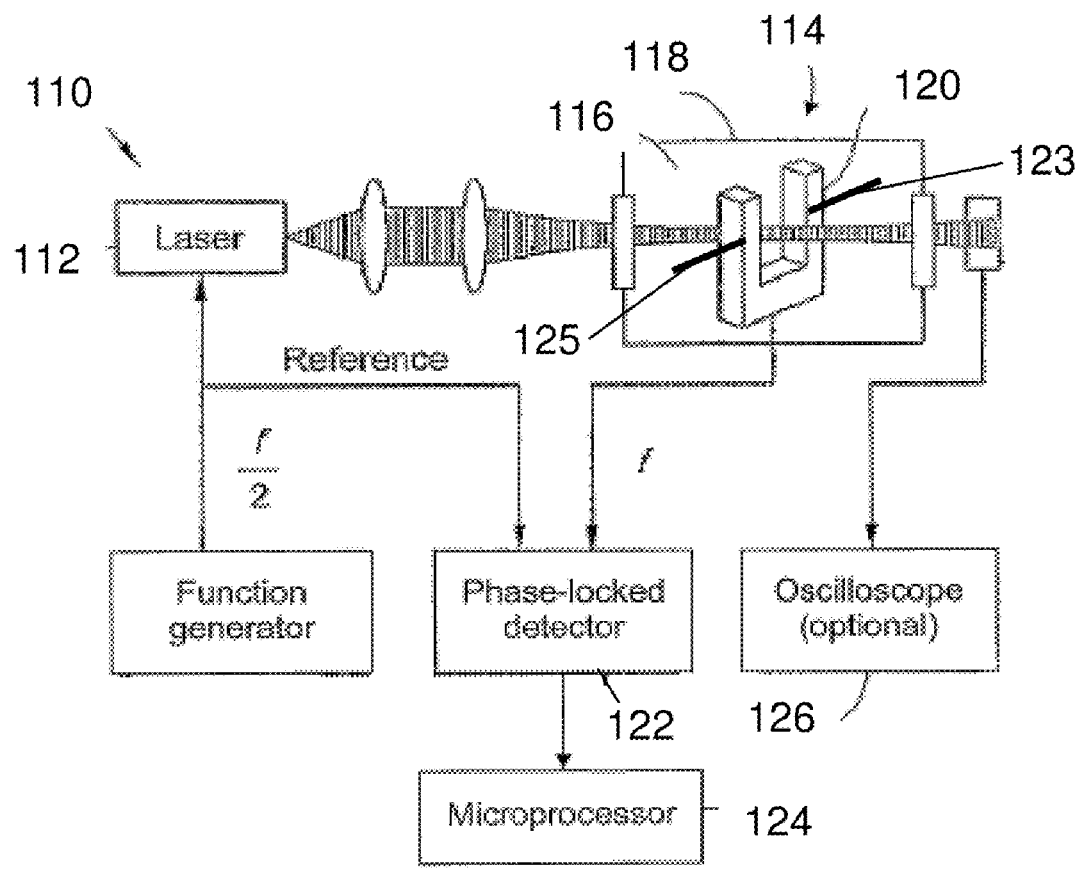
FIG. 2 illustrates an embodiment of a ROTA device.

FIG. 2 illustrates an embodiment of a ROTA device. The device may be configured to apply a modulated light signal to a sample and to detect the resulting optothermoacoustic signal using a phase-locked detector. By way of example, reference is made to FIG. 1, in which a ROTA device 110 comprises a light source 112 configured to emit a beam of radiation into a sample holder 114. The light source 112 may comprise, in a non-limiting example, a laser. Filters may be provided between light source 112 and the sample holder 114 if desired. In addition, the light source 112 may be a modulated light source.

In an embodiment, the sample holder 114 comprises a sample cell 118 containing a sample 116. The sample cell 118 may comprise a number of materials known to persons of ordinary skill in the art. In an exemplary embodiment, the sample cell 118 comprises a material substantially transparent to the wavelength(s) of light emanating from the light source 112. Preferred materials for the sample cell 118 will accordingly vary depending on the wavelengths of light utilized in the spectroscopic apparatus.

The sample 116 may be a fluid or a gas and may substantially fill the sample cell 118. The sample 116 may, for example, comprise a gas stream in which it is desired to detect the presence of a contaminant gas or impurity.

In an embodiment, the apparatus 110 may further comprise an acoustic detector 120. The acoustic detector may be mounted to the cell 118 and may be in acoustic communication with the sample 116. The acoustic detector 120 preferably comprises a transducer such as, for example, a piezoelectric element or a microphone and may be mounted such that a fluid is provided between a surface of the acoustic detector 120 and the cell 118. In the embodiment shown, the acoustic detector 120 may comprise a quartz tuning fork. In alternative embodiments (not shown), the acoustic detector 120 may be another type of detector and may be mounted on the inside or outside the wall of cell 118. The acoustic detector 120 may be removably mounted to the sample cell 118 by, for example, a clamp. The acoustic detector 120 is in electrical communication with a phase locked detector 122, which may be in electrical communication with a microprocessor 124. In certain embodiments, microprocessor 124 processes the incoming signal as described in detail below.

Furthermore, a thermal sensing element 123 may be coupled to one of the tines or portions of the acoustic detector 120 (e.g., a quartz tuning fork (QTF)). In an exemplary embodiment, the acoustic detector 120 may have at least two tines. The thermal sensing element 123 may provide the optothermal functionality to embodiments of the device 110. That is, the thermal sensing element 123 may receive the thermal energy and convert it to mechanical force while the acoustic detector 120 may act as a resonating element and piezoelectric transducer. The thermal sensing element 123 may be used to optimize the sensing device for specific detection tasks using the same detector (such as QTF), and to optimize the detection sensitivity.

In an embodiment, the thermal sensing element 123 may also be coupled to the wall of the cell 118. The thermal sensing element 123 may comprise any material which is sensitive or capable of sensing change in temperature. Non-limiting examples of the thermal sensing element 123 include optical fibers, strips, wires, or combinations thereof. The thermal sensing element 123 may be made of any thermosensitive material. In other examples, the thermal sensing element 123 may comprise porous, gas-permeable cladding, or liquid-permeable cladding. Additionally, the thermal sensing element 123 may be covered by a material increasing adhesion of detected matter from surrounding for higher sensitivity or selectivity, or by material, increasing absorption of radiation when detected matter interacts with it. An optional output device 126 may be included and may be configured to facilitate alignment of the through beam. The output device 126 may comprise, for example, an oscilloscope, or any other suitable device.

Figure 3:
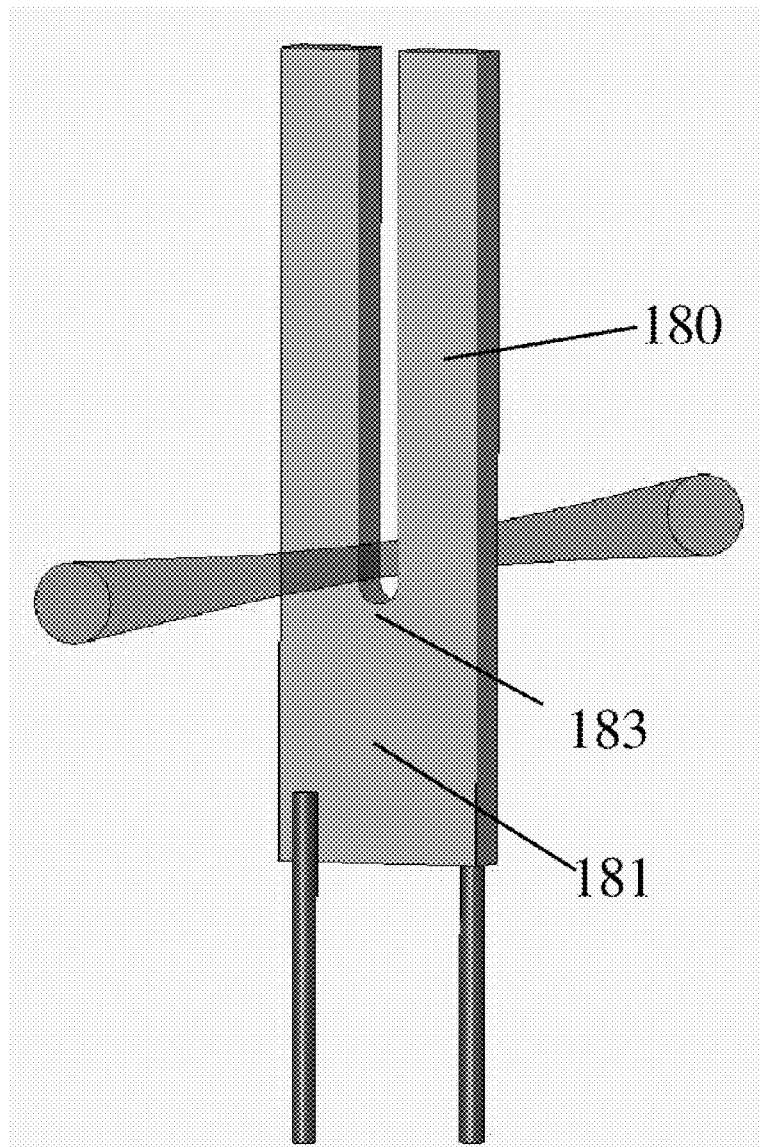
FIG. 3 illustrates another embodiment of a ROTA device.
Figure 4:
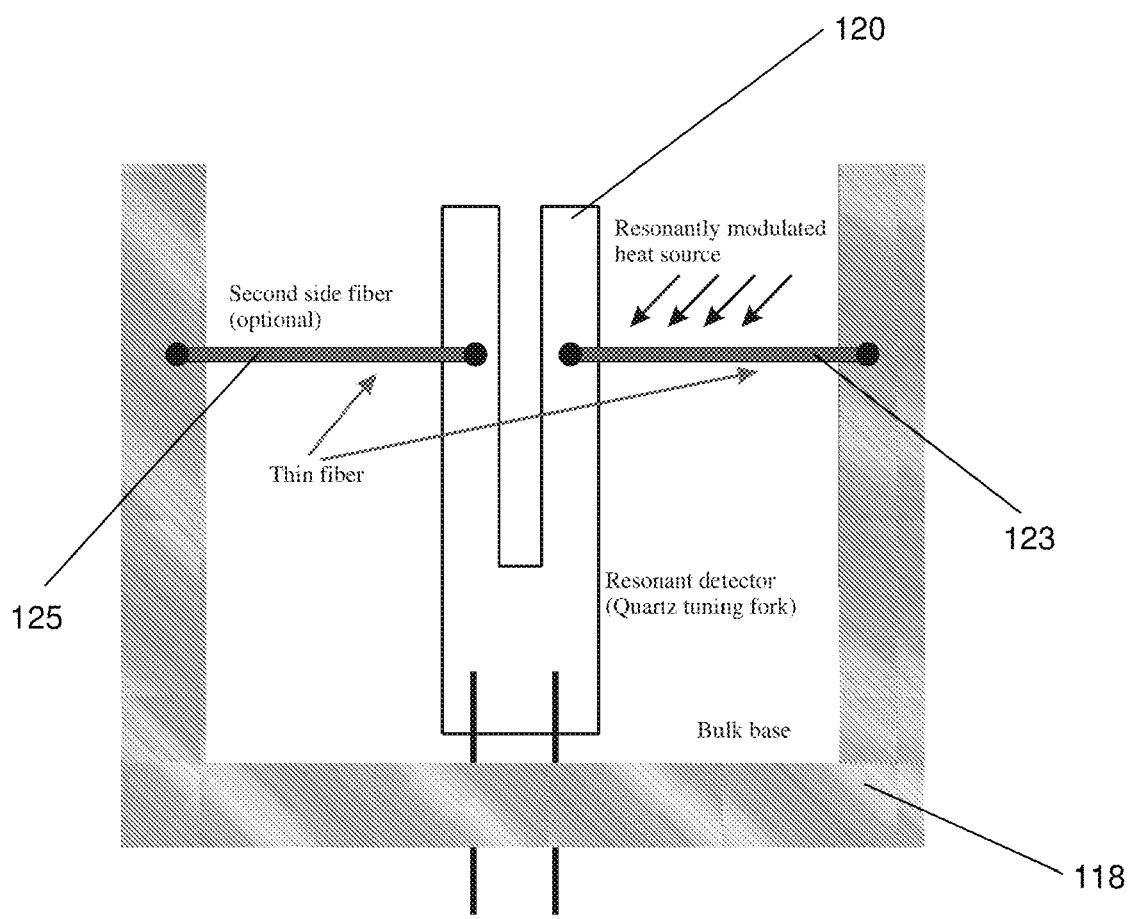
FIG. 4 illustrates another embodiment of a ROTA device.

In an embodiment shown in FIG. 3, the power source is a modulated laser radiation being absorbed by the fluid molecules, fluid is a gas, and the acoustic detector is a QTF 180. The laser beam may be directed between the prongs of the QTF 180 close to where they are merging at the QTF base 181. The junction part 183 of the QTF 180 experiences the most strain during its vibration, and therefore its periodic heating at resonant frequency most efficiently excites the QTF vibration. As such, the thermal sensing element in this case is the QTF junction 183.

The principles of operation of the device 110 are illustrated in FIG. 1. The device may comprise an acoustic detector 120 (e.g., a QTF) and a thermal sensing element 123 (i.e., an optical fiber), both attached to the bulk base or cell 118 as shown. The thermal sensing element 123 may also be attached to one prong or tine of the acoustic detector 120 and stretched between the base 118 and the acoustic detector 120. In an embodiment, a second or additional thermal sensing element 125 may be attached to the second prong of the acoustic detector 120 for symmetrical configuration. In another embodiment, the thermal sensing element 123 may be stretched between the prongs of a QTF.

In an embodiment, though not to be limited as to any particular theory of operation, when the thermal sensing element 123 is heated as a result of optical radiation being absorbed either by the thermal sensing element itself, by the object or matter adjacent or attached to the thermal sensing element, or by some combination thereof, the thermal sensing element tension and hence the force acting upon the QTF prong may be changed. When the excitation stops, the original condition may be restored upon thermal dissipation. In an embodiment where such a heat input is modulated with the resonant frequency of the QTF-thermal sensing element system, mechanical resonant oscillations of the QTF and subsequent generation of the electrical signal may result. The resulting signal may be measured and analyzed to quantify optical absorption.

Accordingly, the method may comprise emitting a modulated beam of light at a wavelength through an acoustic detector and one or more thermal sensing elements, wherein the one or more thermal sensing elements are coupled to the acoustic detector. The method may further comprise determining a resonant frequency of the acoustic detector, wherein the resonant frequency of the acoustic detector is the same as the modulation frequency of the beam of light; and measuring the response of the acoustic detector and the one or more thermal sensing elements to detect the absorbance of a chemical species.

Figure 5:
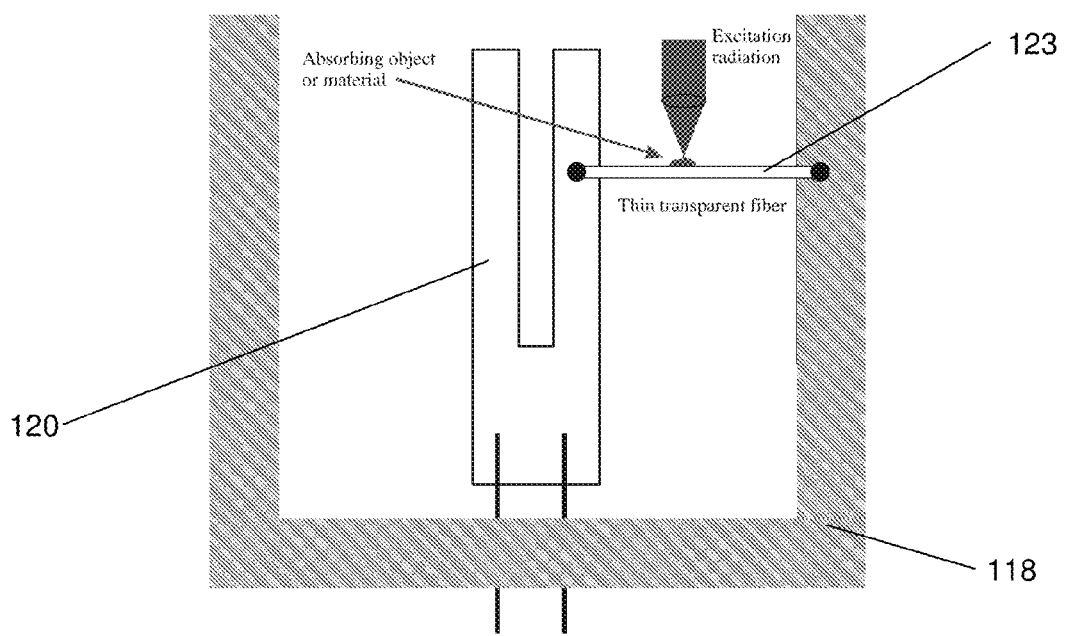
FIG. 5 illustrates an embodiment of a method of detecting optical absorption of a compound.

In an embodiment, the disclosed methods may be used to detect absorption of an evanescent thermal sensing element wave by surrounding gas or liquid media, similar to the embodiment of FIG. 3. In an alternative embodiment, position and absorption intensity for a small object attached to the sensing element (e.g., a carbon nanotube) may be detected when a focused radiation spot is scanned along the thermal sensing element. A particular embodiment is illustrated in FIG. 5, where the technique is applied to detect optical absorption by a microscopic object deposited on the thermal sensing element 123 (e.g., a transparent fiber). The object absorbs periodic laser radiation, the heat is transferred to the thermal sensing element 123 and induces its periodic expansions and contractions. This process excites the QTF vibrations as discussed above.

EXAMPLES

The embodiments having been generally described, the following example is provided as a particular embodiment of the disclosure and to demonstrate the practice and advantages thereof. It is to be understood that the example is presented herein as a means of illustration and is not intended to limit the specification or the claims in any manner.

Referring to FIG. 5, test experiments were carried out using a 25 µm diameter, 5 mm long LF5 glass fiber. Attaching the fiber shifted the resonant frequency from ~32760 Hz to ~33540 Hz as compared to the original bare QTF. Based on the signal, which was generated in the cleanest (least absorbing) sections of the glass fiber by a 20 mW laser at $\lambda=1550$ nm, and the glass manufacturer data, the noise-equivalent limit of detectable fractional absorption was estimated as $2\times10-6$ Hz$-\frac{1}{2}$, or 40 nW·Hz$^{-1/2}$ in terms of average absorbed power for the tested configuration (a smaller fiber will give lower noise). As a result, scanning the focused excitation spot through the fiber length has revealed the presence of many absorbing areas (defects) in the fiber and particles on the fiber surface.

While the preferred embodiments of the invention have been shown and described, modifications thereof can be made by one skilled in the art without departing from the spirit and teachings of the invention. The embodiments described and the examples provided herein are exemplary only, and are not intended to be limiting. For example, possible variations of the disclosed methods and devices may include but are not limited to a non-optical resonant heat input (e.g., as resulting from ionizing radiation), use of the fiber whispering gallery modes to enhance optical field, detection of the sensing element vibrations by optical interferometry, and/or other non-piezoelectric techniques. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. An optical radiation detection device comprising:
   an acoustic detector;
   one or more thermal sensing elements, wherein the one or more thermal sensing elements expand and contract upon absorption and dissipation thermal energy, and wherein the one or more thermal sensing elements are coupled to the acoustic detector so as to impart a mechanical force to the acoustic detector upon the expansion and contraction of the one or more thermal sensing elements; and
   a light source positioned to provide optical radiation to a sample proximate to the one or more thermal sensing elements.

2. The device of claim 1, wherein the acoustic detector comprises a piezoelectric element.

3. The device of claim 1, wherein the acoustic detector comprises a quartz tuning fork.

4. The device of claim 1, wherein the acoustic sensor has an acoustic resonance, vibrational resonance, or combinations thereof.

5. The device of claim 1, wherein the one or more thermal sensing elements is integral to the acoustic detector.

6. The device of claim 1, wherein the light source is positioned such that a beam of light emitted from the light source passes through the acoustic detector.

7. The device of claim 6, wherein the light source is a modulated laser.

8. The device of claim 1, wherein the modulated laser has a frequency ranging from 100 Hz to about 50,000 Hz.

9. The device of claim 1, further comprising a cell at least partially enclosing the acoustic detector and the one or more thermal sensing elements.

10. The device of claim 1, wherein the one or more thermal sensing elements comprises a fiber, a transparent fiber, an optical fiber, a strip, or combinations thereof.

11. The device of claim 9, wherein the one or more thermal sensing elements is coupled to the cell.

12. The device of claim 3, comprising two thermal sensing elements, wherein the quartz tuning fork comprises at least two tines or prongs, and wherein each thermal sensing element is attached to a separate tine or prong of the acoustic detector.

13. A method comprising:
a) directing a beam of light at a sample proximate to a surface of one or more thermal sensing elements, wherein the thermal sensing elements are coupled to an acoustic detector, wherein resonance of the acoustic detector causes the acoustic detector to output an output signal, and wherein the beam of light is characterized as having a wavelength;
b) determining a resonance frequency of the acoustic detector while coupled to the one or more thermal sensing elements via the output signal; and
c) measuring the response of the acoustic detector via the output signal to detect optical radiation absorption of the sample.

14. The method of claim 13, further comprising modulating the beam of light at a frequency, wherein the frequency is about equal to a resonance frequency of the acoustic detector or a sub-harmonic of the resonance frequency of the acoustic detector, wherein the sub-harmonic of the resonance frequency of the acoustic detector is the resonance frequency of the acoustic detector divisible by an integer number.

15. The method of claim 13, wherein the acoustic detector comprises a piezoelectric element.

16. The method of claim 13, wherein the acoustic detector is a quartz tuning fork.

17. The method of claim 16, wherein two thermal sensing elements arc coupled to the quartz tuning fork, wherein the quartz tuning fork comprises two or more prongs or tines, and wherein each of the two thermal sensing elements is coupled to a separate prong or tine of the quartz tuning fork.

18. The method of claim 13, wherein the wavelength of light is selected to effectuate optical radiation absorption proximate to or at the surface of the one or more thermal sensing elements.

19. The method of claim 13, wherein the optical radiation absorption occurs in, on, or about the sample and, wherein the sample comprises a fluid region and/or object.

20. The method of claim 18, wherein the wavelength of light selected is such that the light is absorbed in, on, or about the sample.

* * * * *

UNITED STATES PATENT AND TRADEMARK OFFICE
CERTIFICATE OF CORRECTION

PATENT NO. : 8,102,532 B2
APPLICATION NO. : 12/347470
DATED : January 24, 2012
INVENTOR(S) : Anatoliy A. Kosterev et al.

Page 1 of 1

It is certified that error appears in the above-identified patent and that said Letters Patent is hereby corrected as shown below:

Column 6, line 55, claim 1, add "of" between "dissipation" and "thermal".

Signed and Sealed this
Thirteenth Day of March, 2012

David J. Kappos
*Director of the United States Patent and Trademark Office*